(12) United States Patent
Kulagina et al.

(10) Patent No.: US 8,945,856 B2
(45) Date of Patent: Feb. 3, 2015

(54) AFFINITY-BASED DETECTION OF BIOLOGICAL TARGETS

(71) Applicants: Nadezhda V. Kulagina, Falls Church, VA (US); Chris Rowe Taitt, White Plains, MD (US); George P. Anderson, Bowie, MD (US); Frances S. Ligler, Fuquay Varina, NC (US)

(72) Inventors: Nadezhda V. Kulagina, Falls Church, VA (US); Chris Rowe Taitt, White Plains, MD (US); George P. Anderson, Bowie, MD (US); Frances S. Ligler, Fuquay Varina, NC (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 14/188,784

(22) Filed: Feb. 25, 2014

(65) Prior Publication Data

US 2014/0187446 A1 Jul. 3, 2014

Related U.S. Application Data

(62) Division of application No. 11/307,399, filed on Feb. 6, 2006, now Pat. No. 8,658,372.

(60) Provisional application No. 60/690,046, filed on Jun. 10, 2005.

(51) Int. Cl.
*G01N 33/53* (2006.01)
*G01N 33/569* (2006.01)
*G01N 33/554* (2006.01)
*G01N 33/543* (2006.01)

(52) U.S. Cl.
CPC ...... *G01N 33/56916* (2013.01); *G01N 33/5308* (2013.01); *G01N 33/554* (2013.01); *G01N 33/56911* (2013.01); *G01N 33/56983* (2013.01); *G01N 33/54366* (2013.01)
USPC .......................................................... 435/7.1

(58) Field of Classification Search
None
See application file for complete search history.

(56) References Cited

U.S. PATENT DOCUMENTS

H0001775 H * 1/1999 Ligler et al. ................. 435/7.32

OTHER PUBLICATIONS

Soares et al. (DTIC Technical Reports, Dec. 2004).*

* cited by examiner

*Primary Examiner* — Brian J Gangle
(74) *Attorney, Agent, or Firm* — US Naval Research Laboratory; Joseph T. Grunkemeyer

(57) ABSTRACT

A method of biochemical identification by: providing a plurality of capture species bound to one or more substrates and suspected of having one or more biological targets affinity bound to at least one capture species; detecting which capture species contain bound biological targets to generate a binding pattern; and identifying the biological target based on the binding pattern. The capture species are independently selected from the group consisting of antimicrobial peptides, cytotoxic peptides, antibiotics, and combinations thereof. A device having the capture species bound to the substrates. At least two of the capture species are capable of multi-specific binding to one or more biological targets and may have overlapping but not identical affinity properties.

24 Claims, 10 Drawing Sheets

US 8,945,856 B2

AFFINITY-BASED DETECTION OF BIOLOGICAL TARGETS

This application is a divisional application of U.S. Pat. No. 8,658,372 filed on Feb. 06, 2006 and issued on Feb. 25, 2014, which claims priority to U.S. Provisional Patent Application No. 60/690,046, filed on Jun. 10, 2005. The prior applications and all other publications and patent documents referred to throughout this nonprovisional application are incorporated herein by reference.

BACKGROUND OF THE INVENTION

1. Field of the Invention

The invention is generally related to biological detection.

2. Description of Related Art

With the notable exception of glucose sensors, the vast majority of rapid detection/measurement systems use antibodies for recognition, identification, and quantification of biological targets. Antibody-based detection techniques are powerful, versatile tools for various molecular and cellular analyses, environmental monitoring, and clinical diagnostics. This power originates from the specificity of the antibodies for their particular antigenic sites.

Antibody-based recognition of targets is the basis for detection in many optical and electrochemical biosensors (e.g., interferometers, reflectometric interference spectoscopic sensors, resonance minor sensors, surface plasmon resonance instruments, quartz crystal microbalances, light-addressable potentiometric sensors, electrochemiluminescence systems, fiber optic, and array biosensors), as well as in flow cytometry and non-sensor detection techniques such as lateral flow assays.

Detection techniques employing antibodies, although considered less sensitive than polymerase chain reaction-based systems, are still highly sensitive, are well characterized, and have been adapted for use in rapid assay systems. Due to the specificity of the antibodies, many of these immunoassay-based systems have the additional benefit of requiring little if any sample preparation prior to analysis.

However, assays utilizing antibodies for specific recognition of target analytes have a number of problems that may significantly limit their widespread use in the field: 1) many antibodies are sensitive to environmental temperatures and must be stored frozen, refrigerated, or lyophilized for retention of optimal activity; 2) at least one antibody or set of antibodies is required for each target of interest in multi-plexed assays, increasing the complexity and potential for non-specific or cross-reactive binding; 3) specificity and sensitivity of antibody-based recognition may, in some cases, be mutually exclusive; 4) target-specific antibodies may not be available due to the non-antigenic nature of the analyte; and 5) although monoclonal antibodies are, by their very nature, more consistent than polyclonal antibodies, development and large-scale production of monoclonals is expensive and time-consuming.

The biological detection and clinical diagnostic markets are currently dominated by antibody-based assays. However, antibody-based assays may never be stable enough for long-term sensor applications; such stability is critical for fielding sentry-type systems and for non-laboratory use. Use of antimicrobial peptides and antibiotics should improve the current logistical burdens required of fielded systems.

Many organisms, including mammals, insects, amphibians, fish, crustaceans, plants and bacteria, produce antibiotics and antimicrobial peptides as part of their innate immune systems for protection against invasion by harmful microbes. Antimicrobial peptides and some antibiotics recognize target pathogens by interacting with the microbial cell membranes. Most peptide-membrane and antibiotic-membrane interactions do not involve specific receptors, but rather invariant components of the cell surface; binding is therefore semi-selective—each peptide or antibiotic can bind to multiple microbial species with differing affinities. As natural evolution has conferred upon many of these compounds the stability to withstand adverse conditions (polluted ponds, etc.) and the ability to recognize multiple microbial species, assays using these peptides and antibiotics for recognition should have the following advantages over conventional antibody-based screening methods: stability, resistance to proteases, ability to detect larger numbers of species than a corresponding number of antibodies, and a lower degree of complexity for multi-analyte screening assays.

SUMMARY OF THE INVENTION

The invention comprises a biochemical identification method comprising: providing plurality of capture species bound to one or more substrates suspected of having one or more biological targets affinity bound to at least one capture species; detecting which capture species contain bound biological targets to generate a binding pattern; and identifying the biological target based on the binding pattern. The capture species are independently selected from the group consisting of antimicrobial peptides, cytotoxic peptides, antibiotics, and combinations thereof.

The invention further comprises a device comprising: one or more substrates; and a plurality of capture species bound to the substrates. The capture species are independently selected from the group consisting of antimicrobial peptides, cytotoxic peptides, antibiotics, and combinations thereof. At least two of the capture species are capable of multi-specific binding to one or more biological targets.

BRIEF DESCRIPTION OF THE DRAWINGS

A more complete appreciation of the invention will be readily obtained by reference to the following Description of the Example Embodiments and the accompanying drawings.

DETAILED DESCRIPTION OF THE EXAMPLE EMBODIMENTS

Figure 1:
FIG. 1 shows the effect of fluorophore on non-specific binding in sandwich assays with non-specific binding of Cy5 labeled antibodies

In the following description, for purposes of explanation and not limitation, specific details are set forth in order to provide a thorough understanding of the present invention. However, it will be apparent to one skilled in the art that the present invention may be practiced in other embodiments that depart from these specific details. In other instances, detailed descriptions of well-known methods and devices are omitted so as to not obscure the description of the present invention with unnecessary detail.

The invention may use multiple antimicrobial peptides or other antibiotics as recognition molecules for detection of toxins, viruses, bacteria, rickettsiae, and fungi. The antimicrobial peptides and antibiotics can be used in any detection system in place of antibodies (or other specific receptors) as "capture" species or "tracer" species, as appropriate. A key concept is the use of multiple antimicrobial peptides or antibiotics for target recognition. Based on their overlapping specificities for various targets, a database of different binding patterns can be developed; targets can then be identified based on differences in responses by use of a pattern recognition algorithm. The semi-selectivity of binding can allow detection of a larger number of targets than a corresponding number of antibodies or target-specific receptors. Antimicrobial peptide- and antibiotic-based assays may increase the multi-analyte detection capabilities and improve logistic requirements of current antibody-based detection systems and be amenable to use in any detection platform that currently utilizes antibodies for target recognition.

The method and/or device described herein may differ from other multiplexed peptide- and antibiotic-based detection systems in one or more of the following aspects:

1. The capture species are not combinatorially derived or randomly generated. Rather, they are peptides or antibiotics found in nature, whose binding properties to microbial surfaces (and in some cases, to toxins) may be documented. The capture species are not limited to only naturally occurring anti-microbial peptides and antibiotics, but may also include chimeric peptides, genetic variants, and synthetic mimics.
2. The arrayed capture species have defined secondary structures, unlike combinatorially derived or randomly generated libraries of peptides, aptamers, sugars, etc.
3. Binding of the multiplexed capture species is used to detect bacteria, viruses, fungi, rickettsial targets, and toxins. The detection mechanism is affinity-based, not enzymatically based.
4. The antimicrobial capture species used in the arrays have overlapping specificities. Due to the semi-selective binding characteristics of these molecules, smaller numbers of peptides may be used to detect larger numbers of targets by use of a pattern recognition algorithm to deconvolute data for target identification by these molecules.

Antimicrobial peptides (AMPs) are part of a host's innate immune system in many organisms and serve as the first line of defense against microbial invasion. Highly stable to adverse conditions, AMPs bind semi-selectively to microbial cell surfaces and exert their antimicrobial activity through membrane disruption. Given their ability to bind to multiple target microbes, an array consisting of multiple AMPs can potentially be capable of detecting a higher number of target species than an array with a corresponding number of antibodies. Furthermore, the predicted stability of the AMPs within these arrays is expected to improve operational and logistical constraints over current antibody-based systems. The AMP-based arrays differ from standard peptide arrays in that some or all components are naturally occurring (or derivatives of molecules produced in nature) and may have defined secondary structures, unlike combinatorially derived libraries. Most importantly, as many AMPs have overlapping specificities, the pattern of differences in binding affinities can be used for identification.

One class of AMPs is comprised of linear peptides that naturally fold to form two helical domains: a strongly basic helical region and a hydrophobic helix separated by a short hinge region. Magainins and other amphipathic α-helical AMPs are unstructured in solution, but become helical upon interaction with target membranes. Because of its stability and ability to bind to multiple bacterial species magainin I (GIGKFLHSAGKFGKAFVGEIMKS (SEQ ID NO 12)) may be used as a recognition molecule for incorporation into an array-based sensor for detection of pathogenic bacteria.

In general, use of multiplexed antimicrobial peptides and antibiotics for target detection may possess the following advantages over standard antibody-based detection techniques:

1. Equivalent or superior detection of target analytes. This has already been demonstrated with botulinum toxoid, but will depend on the binding constants of each recognition molecule for the targets.
2. Superior storage characteristics. Antibody-based and DNA-based detection systems are logistically burdensome. As many antimicrobial peptides and antibiotics have evolved for survival in active form in the environment, it is anticipated that activity will be retained under harsher conditions than can be used with conventional antibody-based techniques
3. Capability for simultaneous detection and identification of a larger number of targets than a corresponding number of antibodies or nucleic acid probes. Due to the overlapping, semi-selective binding characteristics of the peptides and antibiotics, fewer of these recognition molecules will be needed to detect large numbers of targets.
4. Potential for therapeutics and/or decontamination. The pattern of binding may be indicative of sensitivity of target bacteria, rickettsiae, and fungi to various antibiotics and antimicrobial peptides.

Since the invention does not rely on a single transduction mechanism (e.g., amperometric detection of an enzymatic product), the invention may be adaptable from fluorescence to other detection systems. The invention may use antimicrobial peptides and antibiotics for either capture and tracer elements or both. The multiplexed antibiotics and/or peptides can also be used in conjunction with antibodies and other recognition species in either orientation.

Factors that may lead to optimal performance include but are not limited to: 1) direct immobilization of capture peptides/antibiotics onto sensor substrates; 2) use of selected fluorophores; and 3) use of a second bead when using peptides/antibiotics as tracers. It is possible that these factors may vary depending on the detection platform used with the multiplexed antimicrobial peptides and antibiotics.

The device and method may be used with a variety of capture species and biological targets. Suitable biological targets include, but are not limited to, bacteria, fungi, viruses, rickettsiae, toxins, and combinations thereof. Suitable capture species include, but are not limited to, alamethicin, peptaibols, apidaecin, bacitracin, bactenecins, bombinin, brevinin, buforins, cathelicidins, cecropins, cepaphalosporins, cytolysins, dermaseptins, defensins, esculentins, gramicidins, hemolysins, histatin, indolicidins, beta-lactams, lactoferricin, nisin, lantibiotics, magainins, mastoparans, melittin, moricin, parasin, pediocin, penicillins, polymyxins, protegrins, ranalexin, streptogamins, tachyplesins, teichoplanin, thionins, vancomycin, vibriolysins, derivatives thereof, and combinations thereof. Any number of the capture species may be naturally occurring peptides. For example, one, a majority, or all of the capture species may be naturally occurring peptides.

The capture species may be part of an innate immune system providing chemical immunity. They may have, but are not limited to, 12-45 amino acids. They may bind to components of a microbe's surface to disrupt to the membrane. This may require multiple peptides interacting with the membrane and require peptide-peptide interactions. They may use semi-selective binding in that the peptide-surface interaction may occur across different genera, but the strength of interaction varies according to the membrane composition and presence or absence of different membrane components.

Not all interactions between AMPs and membranes of target organisms are fully characterized, but they have been demonstrated to occur in the absence of specific receptors. Cationic peptides are thought to preferentially interact with negatively charged phospholipids on bacterial and fungal membranes, with only marginal activity against zwitterionic phospholipids. Most cationic peptides therefore exhibit selective toxicity for bacterial, fungal, and protozoan targets, rather than mammalian ones, and may preferentially interact with Gram-negative bacteria over Gram-positive species. On the other hand, AMPs with hydrophobic segments (e.g., melittin, alamethicin) are highly toxic to mammalian cells but also bind with high affinity to bacterial membranes. Table 1 shows some example AMPs.

TABLE 1

Sequences and structures of select antimicrobial peptides (AMPs)

Non-ribosomally synthesized

| | |
|---|---|
| Alamethicin | Ac-UPUAUAQUVUGLUPVUUEQF-OH (SEQ ID NO: 1)<br>U = methylalanine |
| Polymyxin B | fa-BTBBBFLBBT (SEQ ID NO: 2)<br>fa = fatty acid  B = diaminobutyrate |
| Polymyxin E (colistin) | fa-BTBBBLLBBT (SEQ ID NO: 3)<br>fa = fatty acid  B = diaminobutyrate |
| Gramicidin A | fo-XGALAVVVWLWLWLW-Et (SEQ ID NO: 4)<br>fo = formyl  X = V,I  Et = ethanolamine |
| Bacitracin | I(C)LEIKOIFHDN (SEQ ID NO: 5)<br>O = ornithine |

Amphipathic α-helical

| | |
|---|---|
| Buforin II | TRSSRAGLQFPVGRVHRLLRK (SEQ ID NO: 6) |
| Cecropin A | KWKLFKKIEKVGQNIRDGIIKAGPAVAVVGQATQIAK-CONH$_2$ (SEQ ID NO: 7) |
| Cecropin B | KWKVFKKIEKMGRNIRNGIVKAGPAIAVLGEAKAL (SEQ ID NO: 8) |
| Cecropin P1 | SWLSKTAKKLENSAKKRISEGIAIAIQGGPR (SEQ ID NO: 9) |
| CecA/Mel hybrid | KWKLFKKIGIGAVLKVLTTG-CONH$_2$ (SEQ ID NO: 10) |
| Dermaseptin | ALWKTMLKKLGTMALHAGKAALGAAADTISQGTQ (SEQ ID NO: 11) |
| Magainin I | GIGKFLHSAGKFGKAFVGEIMKS (SEQ ID NO: 12) |
| Magainin II | GIGKFLHSAKKFGKAFVGEIMNS-CONH$_2$ (SEQ ID NO: 13) |
| Melittin | GIGAVLKVLTTGLPALISWIKRKRQQ-CONH$_2$ (SEQ ID NO: 14) |

β-Sheet/β-loop

| | |
|---|---|
| Bactenecin (intramolecular disulfides) | RLCRIVVIRVCR (SEQ ID NO:15) |
| Nisin (intramolecular thioethers) | IXAIULAZPGAKZGLAMGANMKZAZAHASIHVUK (SEQ ID NO: 16)<br>U = 2,3-didehydroalanine  X = 2,3-didehydrobutyrine<br>Z = α-aminobutyrate |
| Defensin HNP-1 (intramolecular disulfides) | ACYCRIPACIAGERRYGTCIYQGRLWAFCC (SEQ ID NO: 17) |

The mechanism of membrane disruption is believed to occur by formation of either "carpets" or channels. The "carpet" mechanism involves binding of charged (typically cationic) amino acids to headgroups of membrane phospholipids or lipopolysaccharide. After initial binding, AMPs aggregate to form a "carpet," with helices or β-sheets oriented parallel to the membrane surface. Upon rotation of the AMP chains, hydrophobic side chains are inserted into the membrane, disrupting lipid packing, or alternatively, creating a toroidal pore. Channel formation, on the other hand, involves insertion of the peptide backbone into the membrane, rather than the side chains. After insertion of the peptide backbone into the membrane, AMPs aggregate to form a barrel-like structure with a central aqueous channel. A feature of both mechanisms is the requirement for multiple AMPs and for peptide-peptide interactions. The attached claims are not intended as requiring these or any other mechanisms.

Not every species on the substrates is required to be a capture species. A device may be an array having additional species, including but not limited to, antibodies, for simultaneously performing other types of assays. In a device, there are at least two capture species that are capable of multi-specific binding. There may also be 3, 4, 5, 10, 20, 50, or 100 or more such capture species. Optionally, at least two of the capture species have overlapping, but not identical affinity properties.

The biological target or targets may be bound to the capture species by exposing the substrate or substrates to a sample suspected of containing the biological target and allowing the target to bind to the capture species. In one embodiment, the biological target may be directly detected by a reagent-less assay. Such assays include, but are not limited to, opto-electronics, surface plasmon resonance, interferometry, and quartz crystalline microbalance. A reagent may also not be needed when the target has a label attached to the target that is capable of producing an opto-electronic signal.

In another embodiment, the presence of the biological target is detected by use of a tracer species that comprises a recognition element capable of binding to the biological target and a signal generating element. The substrate is exposed to one or more such tracer species, which are allowed to bind to the bound biological target. Detecting the biological target is done by detecting the tracer species bound to it. The device may include a reservoir or source of the tracer species. Alternatively, the tracer species may be bound to the biological target before the target is bound to the capture species.

Among other possibilities, the signal generating element may be capable of producing an opto-electronic signal, such as fluorescence. Suitable signal generating elements include, but are not limited to, fluorophores, chromophores, fluorophore-labeled species, chromophore-labeled species, fluorescent nanospheres or microspheres, an enzyme or catalyst capable of producing an opto-electronic signal, and fluorescent nanospheres or microspheres coated with one of the capture species. Suitable fluorophore labels include, but are not limited to, Cy3, Cy5, cyanine dyes, phycobili proteins, and fluorescent protein. The tracer species may also be a fluorescent nanosphere or microsphere coated with a capture species, particularly when used with the LUMINEX® system. As used herein, the terms "nanosphere" and "microsphere" are defined as used anywhere in the relevant art, as opposed to defining strict dimensions. The tracer species may also be a stain applied to one or more biological targets, either before or after binding to the capture species. Such staining assays are described in Ligler et al., U.S. Pat. No. 5,496,700.

In one embodiment, the substrate may be any flat surface, such as those used in the microarray art, including but not limited to, a glass slide. The surface of the substrate may be functionalized with a crosslinker, with the capture species covalently bound to the crosslinker. Alternatively, the capture species may be non-covalently bound to the substrate, or may be bound to a carrier protein or scaffold, which is covalently or non-covalently bound to the substrate.

In this embodiment, the different capture species may be bound in separate regions of the substrate. When a biological target or tracer species is detected at a particular place on the substrate, it can be determined in which region the target is located, and thus, to which capture species the target is bound. The regions need not be discrete or disjoint, as long as it can be determined on which capture species a detection event is located.

The NRL array biosensor generally uses sandwich fluoroimmunoassays performed on the surface of an optical waveguide (microscope slide) to detect targets of interest. Typically, biotin-labeled "capture" antibodies are immobilized in a patterned array on an avidin-coated slide. After sample is flowed over the array, bound target is detected with a fluorescently labeled "tracer" antibody, whose presence and location are determined using a camera system.

This embodiment of the invention may use an array of multiple antimicrobial peptides and antibiotics. Typical peptide/antibiotic immobilization procedures include (but are not limited to) the following steps:

1. Cleaning of microscope slides using standard methods (KOH in alcohol or $H_2SO_4$)
2. Silanization with amino-functional or thiol-functional silane
3. Treatment with homo- or hetero-bifunctional crosslinker ($BS^3$, GMBS)
4. Placement of a patterning template onto the treated surface
5. Overnight incubation with 1-10 mg/mL peptide/antibiotic in buffer
6. Washing of the surface, followed by blocking, drying and storage Direct assays were performed by flowing fluorescently labeled target (cells, toxins, etc.) over the surface of the slide and washing away unbound target. Sandwich assays were performed by flowing (unlabeled) sample over the slide, washing, flowing over a fluorescent tracer antibody, and washing a second time; antibiotic or peptide can also be used as a tracer molecule.

In another embodiment, a plurality of microspherical substrates is used, such as in the LUMINEX® system. There are subsets of microspheres comprises a different capture species or combinations there of bound its the surface. Each microsphere is encoded by two dyes. The ratio of the dyes is determined by the identity of the capture species.

The LUMINEX®$^{100}$ is a commercial flow cytometer that performs sandwich immunoassays on the surface of microspheres encoded by different ratios of two long wavelength dyes. Up to 100 simultaneous assays can be performed, as LUMINEX® can distinguish between the different bead types. The current embodiment using antimicrobial peptides and antibiotics may require a dual-bead assay for target detection.

In a typical assay, antibody-coated LUMINEX® beads (antibody immobilized by avidin-biotin interactions) are added to the sample containing the target species; these beads could potentially be coated with antibiotics or antimicrobial peptides. After the target has bound to the capture beads, fluorescent nanospheres coated with antimicrobial peptide are added to the sample. After a short incubation, the sample is then centrifuged to pellet both the nanospheres and the microspheres. The beads are then resuspended by a short exposure in an ultrasonic bath and then sample is directly measured by the LUMINEX® flow cytometer.

For both systems, it was found that the antimicrobial peptides/antibiotics may bind targets more efficiently if they are covalently attached to a surface. This is in contrast to many antibody-based detection systems that allow immobilization via avidin-biotin interaction. Although the immobilization chemistry used in these examples provides higher levels of binding, the method of immobilization may be modified as appropriate for the detection platform. Furthermore, the peptides and antibiotics can be attached to beads, proteins, dendrimers, etc. for capture and detection of target analytes.

Characteristics of surface chemistry for the immobilization typically considered as disadvantages in other systems (e.g., lack of diffusion, steric hindrance) were advantageous when immobilizing the peptides and antibiotics. Tight control over orientation of the molecule on the surface and prevention of over-labeling may be significant when using antimicrobial peptides and antibiotics. Furthermore, due to the requirement for strong target interactions, valency (density on the surface) may also be relevant in endowing peptide-based systems with sufficient strength to capture the target species. This may also explain why high molar quantities of peptides were required in the immobilization step in the examples (0.2-2 mM versus <1 µM typically used with antibodies) and why avidin-biotin-based immobilization may not be sufficient for tight binding.

Figure 2:
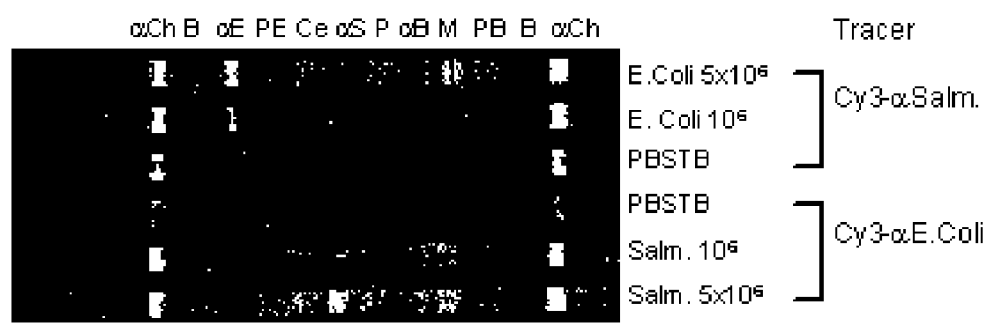
FIG. 2 shows the effect of fluorophore on non-specific binding in sandwich assays in detection of *E. Coli* and *Salmonella* on a multipeptide array with Cy3 labeled antibodies.

For the examples discussed herein, the amount of non-specific binding by tracer species was affected by the fluorophore used. Cy5—or ALEXA FLUOR® 647—labeled tracer species bind non-specifically to immobilized peptides and antibiotics, regardless of the presence of target analyte (FIG. 1, PBSTB lanes). However, it was determined that tracers labeled with Cy3 dye (in which the alkene chain is two carbon units shorter) do not bind non-specifically (FIG. 2, PBSTB lanes); it was successfully demonstrated that sandwich assays using Cy3-labeled tracers can be used to detect multiple targets. The use of Cy3 for successful sandwich assays was surprisingly advantageous, given the similarity in structure of the dyes. Although this dye was suitable for successful sandwich assays using the NRL array sensor, other systems may require different fluorophores and additional optimization.

Figure 12:
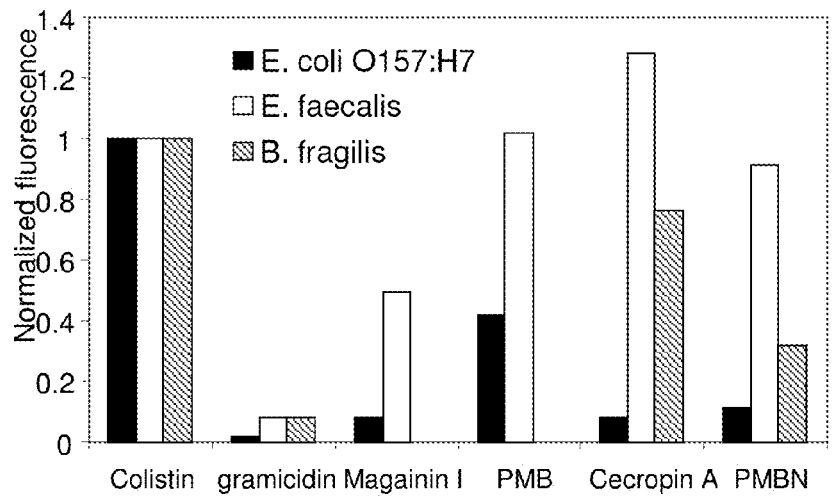
FIG. 12 shows patterns of binding by *E. coli* ($10^6$ cfu/ml), *E. faecalis* ($10^4$ cfu/ml), and *B. fragilis* ($10^5$ cells/nil), in LUMINEX® AMP—tracer assays. Values normalized to colistin signals.
Figure 13:
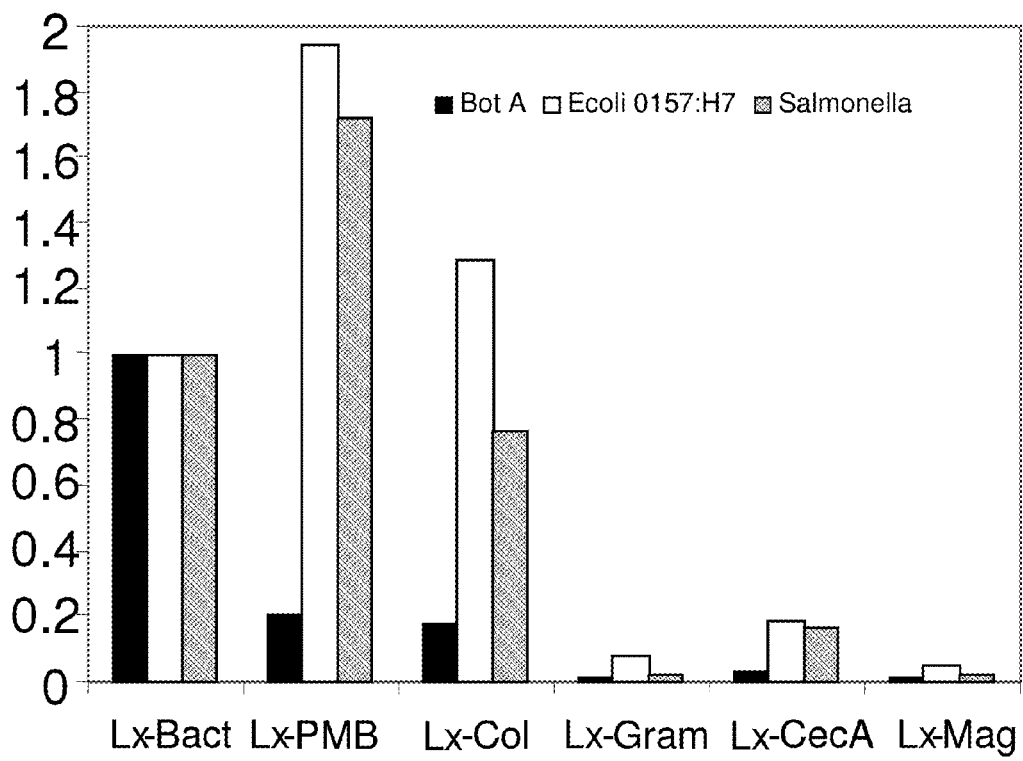
FIG. 13 shows binding patterns for LUMINEX® AMP capture—*E. coli, Salmonella* ($10^6$ cfu/ml each), bot toxoid A (10 µg/ml).
Figure 14:
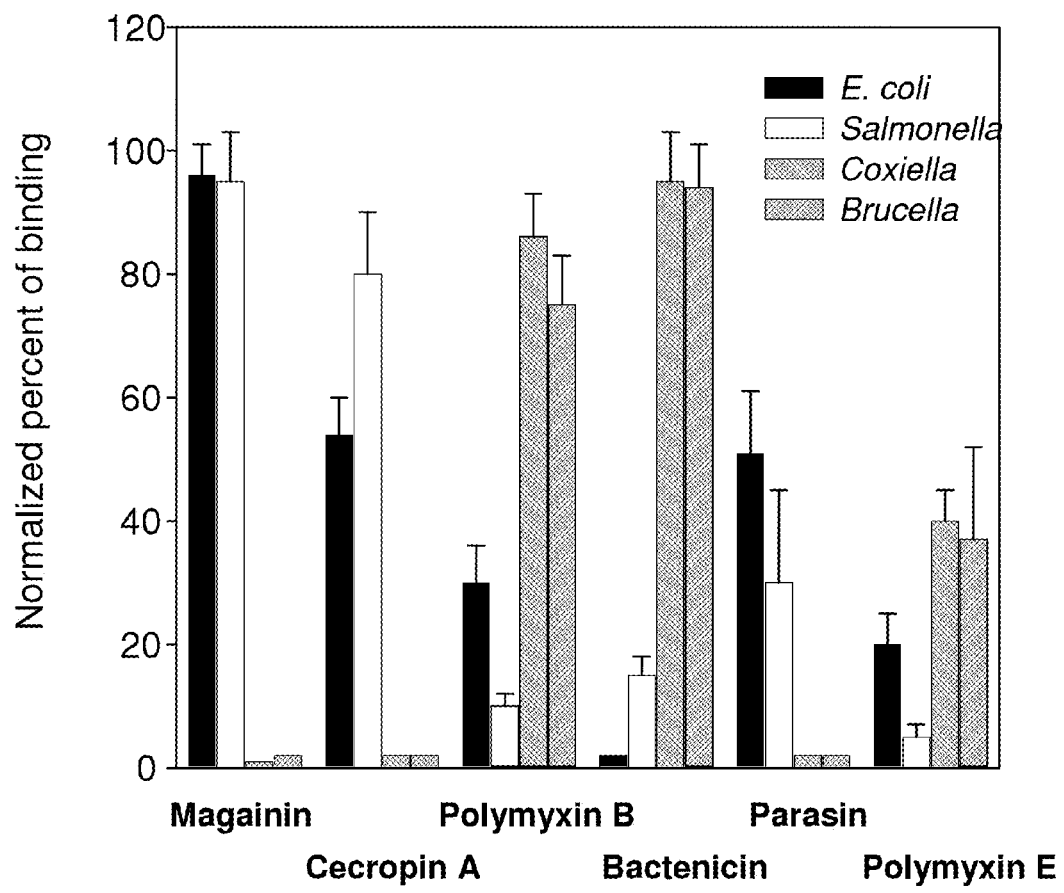
FIG. 14 shows binding patterns for Array Biosensor—*E. coli, Salmonella* ($10^6$ cfu/ml each), *C. burnetti* ($2\times10^6$ cells/ml), *Brucella* ($5\times10^4$ cfu/ml).

A detector may be used to independently detect the presence of the tracer species or the biological target in each region to generate a binding pattern, such as those shown in FIGS. 12-14. The type of detector used is dependent on the type of signal generated by the target or tracer. The pattern describes to which capture species, and to what degree, the biological target or targets has bound. The pattern may then be compared to a database of known binding patterns to identify the biological target. The identification may be done by performing a pattern recognition algorithm using a database of at least one of the biological targets characterizing the biological target by its relative binding affinity for at least one of the capture species. This algorithm may be performed with a system such as a computer.

Figure 3:
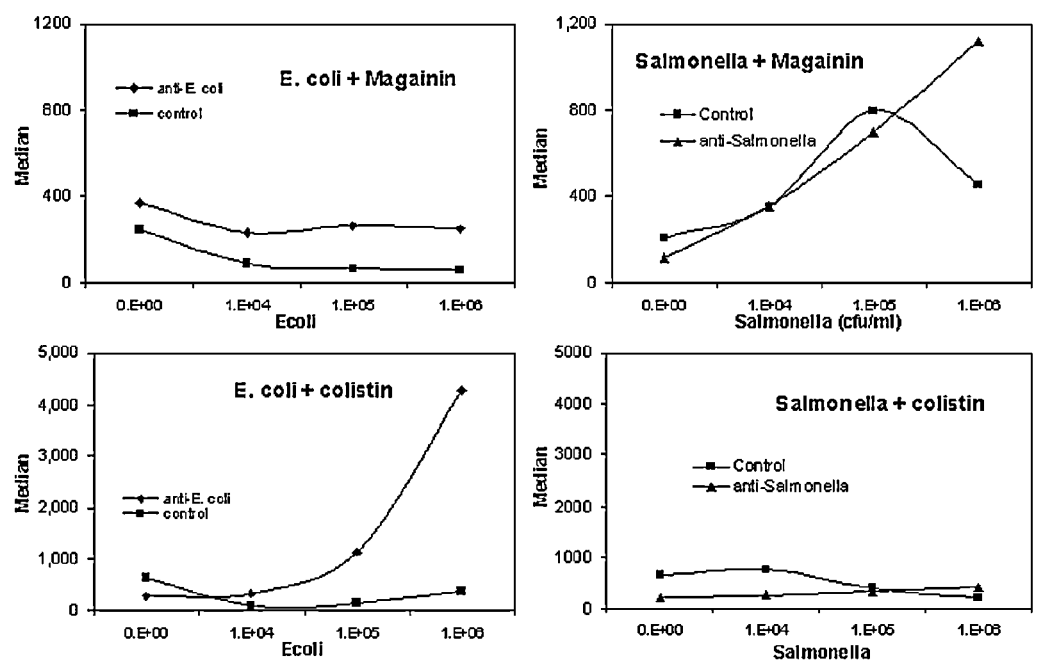
FIG. 3 shows different binding patterns of *E. coli* and *Salmonella* to various peptides and antibiotics—LUMINEX®[100].
Figure 4:
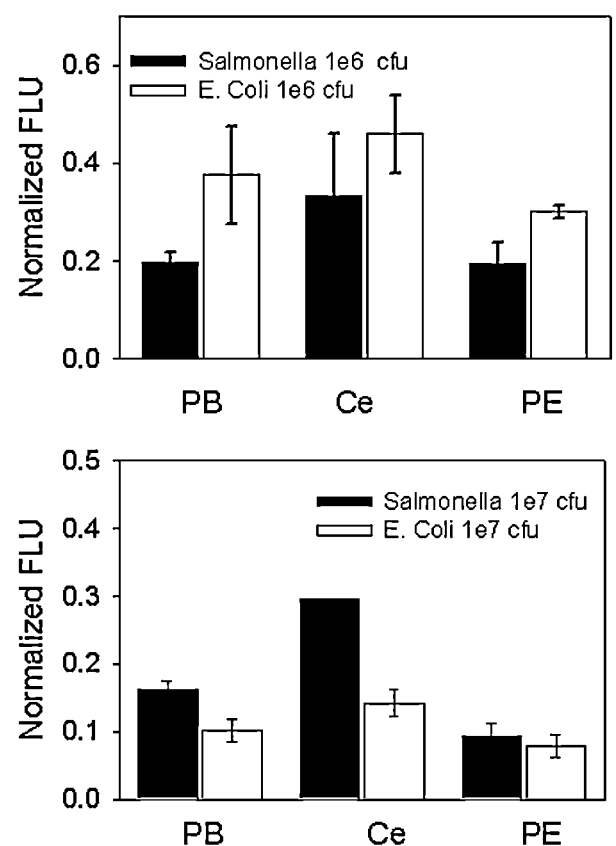
FIG. 4 shows different binding patterns of *E. coli* and *Salmonella* on various peptides and antibiotics—Array Biosensor.

The invention can be adaptable to multiple detection platforms, including biosensors. Bacteria were successfully detected on NRL's array biosensor and the LUMINEX®[100]. Species-specific binding patterns of sets of peptides using both LUMINEX® (FIG. 3) and the NRL array sensor (FIG. 4) were demonstrated. These results further demonstrate the proof-of-principle that the pattern of binding can be used to distinguish different targets.

Figure 5:
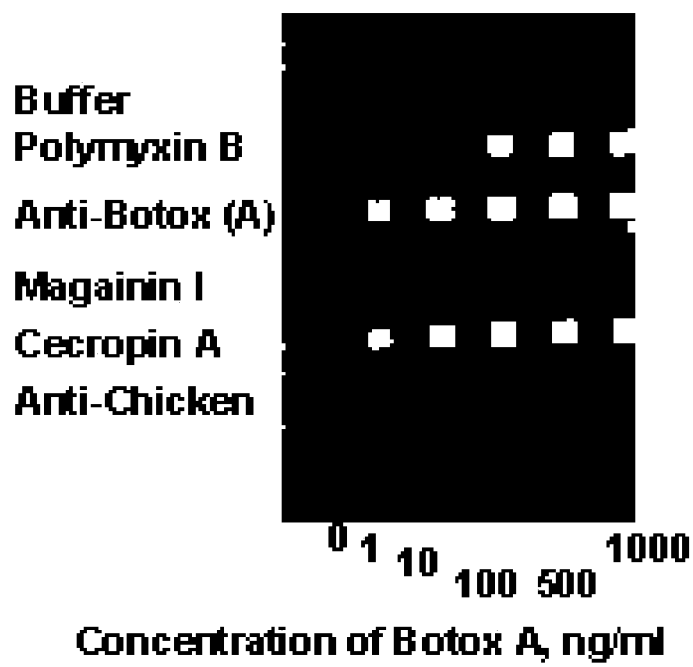
FIG. 5 shows detection of a toxin using multiplexed antibiotics and antimicrobial peptides. Botulinum toxoid bound to Cecropin A and (less strongly) to polymyxin B, but not to magainin.

It was also demonstrated that the invention can be used for detection of non-bacterial targets. FIG. 5 shows detection of botulinum toxoid A using various immobilized antimicrobial peptides and antibiotics, as well as an appropriate anti-botulinum antibody. The estimated limit of detection observed in the peptide-based assays (specifically, in the cecropin lane) was significantly lower than previously observed for antibody-based assays. This is also evident in the higher signals shown in FIG. 5. Although inhibition of botulinum toxin by buforin has been reported (Garcia et al., "Buforin I, a natural peptide, inhibits botulinum neurotoxin B activity in vitro," *J. Appl. Toxicol.*, 19(S1), S19-S22 (1999)), the use of other antimicrobial peptides and antibiotics for toxin detection was not obvious; their typical mode of action and interactions is by membrane interaction. These results demonstrate that the invention may have additional uses in detection of other (non-microbial) targets.

At least a 10-fold improvement in detection limit was observed over prior art for detection of botulinum toxoid A. Various targets (*Salmonella, E. coli*) were distinguished based upon their pattern of binding to different peptides. It is anticipated that the pattern of binding can be used to identify significantly more bacterial (and potentially fungal, viral, and toxic) targets.

The invention can allow sensitive detection of bacterial cells or cell fragments in a rapid biosensor assay using antimicrobial peptides for target recognition. Furthermore, this study demonstrates proof-of-concept that these simple 70-minute AMP-based assays provided similar detection limits but greater stability at room temperature than analogous antibody-based assays. These assays can enable creating a multiplexed detection platform that uses the semi-selective binding of multiple AMPs to detect large numbers of bacterial species. Preliminary evidence that the directly immobilized magainin shows semi-selective binding characteristics; only trace binding of Campylobacter sp. and Bacillus sp. was observed under analogous conditions.

Having described the invention, the following examples are given to illustrate specific applications of the invention. These specific examples are not intended to limit the scope of the invention described in this application.

EXAMPLE 1

Figure 6:
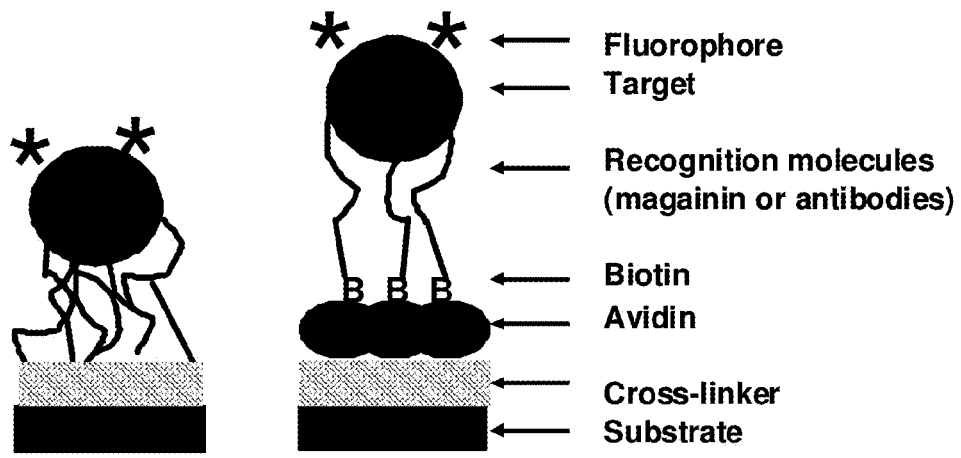
FIG. 6 schematically illustrates immobilization of AMPs on a glass slide followed by binding of a fluorescent target.

Array Biosensor—Immobilization of peptides and antibodies—FIG. 6 schematically illustrates immobilization of AMPs on a glass slide followed by binding of a fluorescent target. The direct method has attachment of recognition molecules to the substrate through cross-linking chemistry with GMBS. Indirect immobilization has attachment of recognition molecules to the substrate through an avidin-biotin interaction. The immobilization methodology utilizes sequential incubations with a thiol-terminated silane, the heterobifunctional crosslinker N-[γ-maleimidobutyryloxy]-succinimide ester (GMBS), and a protein or peptide containing one or more primary amines. Briefly, standard soda-lime microscope slides (Daigger, Vernon Hills, Ill.) cleaned with 10% KOH (w/v) in methanol were treated for 1 hour, under nitrogen, with a 2% solution of 3-mercaptopropyl trimethoxysilane in toluene. The slides were then rinsed with toluene, dried under nitrogen, and incubated for 30 minutes in 1 mM GMBS crosslinker (Pierce, Rockford, Ill.) in absolute ethanol. Following the crosslinker incubation, magainin I and control antibodies were immobilized on the surface using either 1) indirect attachment via avidin-biotin interactions (covalent attachment of an avidin derivative, followed by incubation with biotinylated magainin or antibody), or 2) direct covalent attachment chemistry (interaction of succinimidyl ester with primary amines on the antibody or magainin).

For avidin-biotin-mediated attachment of capture molecules, the slides were removed from crosslinker, rinsed briefly in water, and then incubated overnight in 33 µg/mL NeutrAvidin (Pierce, Rockford, Ill.) in phosphate buffered saline, pH 7.4 (PBS). The NeutrAvidin-treated slides were rinsed in PBS and stored at 4° C. in PBS until patterned with biotinylated capture species. Patterning of capture species onto NeutrAvidin-coated slides was performed by placing a 6-channel poly(dimethylsiloxane) (PDMS) patterning template onto the surface of each slide and filling each channel with an appropriate biotinylated capture molecule in PBS. Following overnight incubation at 4° C., each channel was emptied and rinsed with PBS. Slides were then blocked for 30 minutes in 10 mg/mL gelatin, rinsed with nanopure water, and dried under nitrogen. The following capture species were patterned on NeutrAvidin-coated slides: (1) 1 mg/mL (0.4 mM) custom synthesized magainin I possessing a C-terminal biotin; (2) 1 mg/mL (0.4 mM) magainin I labeled with an amine-specific biotin derivative; and (3) 10 µg/mL (66 nM) biotinylated control antibodies.

For direct covalent attachment of recognition molecules, slides were removed from crosslinker, rinsed briefly in water, dried, and then placed in contact with the PDMS patterning templates. Unlabeled antibodies (10 µg/mL in PBS) and magainin I (1 mg/mL in PBS) were injected into appropriate channels and incubated overnight at 4° C. The channels were then emptied and rinsed with PBS. Patterned slides were blocked with 10 mg/mL gelatin as above, dried, and stored at 4° C. for up to 2 weeks.

Biotinylation of capture molecules—Rabbit anti-*E. coli* 0157:H7 (KPL, Gaithersburg, Md.), anti-*S. typhimurium* (Biodesign, Saco, Me.), and anti-*Listeria* (Biodesign, Saco, Me.) were biotinylated with a 5-fold molar excess of the long-chain derivative of biotin N-hydroxysuccinimidyl ester (EZ-Link NHS-LC-biotin, Pierce) according to the following procedure.

1. Calculate the amount of biotin-LC-NHS ester needed to for 5:1 (biotin:antibody) ratio.
2. Dilute antibody solution such that the final concentration is 1-2 mg/ml. (As the reaction chemistry links biotin (or Cy5) to the antibody via amine groups, the antibody must be in a buffer that does not contain moieties. Amine-based buffers (e.g., Tris, glycine) must be removed from the antibody prep prior to the labeling reaction. Any method suitable for desalting may be used for buffer exchange.)
3. Add ⅑ volume of 0.5 M bicarbonate buffer, pH 8.5 to the antibody solution such that the final bicarbonate buffer is 50 mM.
4. Dissolve biotin-LC-NHS ester in DMSO to a final concentration of 1 mg/ml.
5. Add the biotin/DMSO mix to the diluted antibody in bicarbonate buffer, such that the final biotin to antibody ratio is 5:1.
6. Incubate the antibody/biotin mix at room temperature for 30 minutes while rocking.
7. Pipette mix onto a Bio-Gel P-10 column, which has been pre-equilibrated in PBS (The Bio-Gel P-10 column is prepared by first suspending Bio-Gel P-10 gel (medium, 90-180 µm) into PBS to make a slurry. To completely hydrate the Bio-Gel, allow the slurry to sit overnight at room temperature or alternatively, autoclave or boil for 20 minutes. The hydrated slurry is stable at room temperature for months. Immediately prior to loading the column, the slurry is degassed by application of a vacuum. The slurry is then loaded into a 25 ml column, pre-filled with approx. 3 ml PBS. Once the column has been filled, it is then flushed with at least three volumes of PBS. After the elution of the conjugate products, the column must be flushed exhaustively with PBS and stored wet (PBS) at room temperature for future used.). Allow the sample to soak into gel. Rinse top of gel and sides of column with PBS.
8. Add a layer of 1-5 ml PBS onto the top of gel and monitor the absorbance of the eluent at 280 nm. Collect all eluent by fractions and save the first peak. Add more PBS buffer as necessary
9. Dilute an aliquot of the first peak fraction with PBS (typically 10×dilution) and measure the absorbance at 280 nm.
10. Determine the concentration of the biotinlylated conjugate and store at 4° C. The absorbance at 280 nm should be below a value of 1.0 absorbance units for accurate determination of concentration. The concentration of biotinylated antibody is determined by the Beer Lambert Law ($A=\epsilon c l$), with $\epsilon_{280\ nm,\ 1\ mg/ml,\ 1\ cm} = 1.4$.

Unlabeled magainin I (GIGKFLHSAGKFGKAFVGEIMKS (SEQ ID NO 12), AnaSpec, San Jose, Calif.) was incubated with EZ-Link NHS-LC-biotin at a 1:1 (biotin:peptide) molar ratio in PBS for 24 hours at room temperature; the biotin was first dissolved in a small volume of dimethylsulfoxide (DMSO) prior to adding to the labeling mix. After 24 hours incubation, samples were loaded into dialysis tubing (1000 MWCO) and dialyzed against PBS over 3 days, with 6 changes of buffer. The biotinylated magainin I was characterized by electrospray mass spectrometry using a QSTAR pulsar I (Applied Biosystems, Foster City Calif.) with nanoflow direct infusion. A custom-synthesized magainin possessing a C-terminal biotin (99% pure, purchased from SynPep, Dublin, Calif.) was also used in this study.

Preparation of fluorescent cells—Heat-killed *S. typhimurium* and *E. coli* O157:H7 cells (KPL) were rehydrated in PBS as recommended by the manufacturer. Approximately $10^8$ cells/mL were incubated for 30 min in 50 mM sodium borate, pH 8.5, with one packet of Cy5 bisfunctional N-hydroxysuccinimidyl ester (Amersham, Arlington Heights, Ill.) dissolved in 25 µL anhydrous DMSO immediately before use. Labeled cells and unincorporated dye were loaded into dialysis tubing (1000 MWCO) and dialyzed overnight at 4° C. against 3 changes of PBS. Labeled cells were then removed from the bag and stored in the dark at 4° C. until use.

Assay Protocol—Patterned slides were placed in contact with PDMS assay templates molded to contain 6 channels oriented orthogonal to the channels in the patterning templates. The slides with the attached assay templates were connected to a multichannel peristaltic pump at one end of each flow channel via syringe needles (outlet). The opposite end of each flow channel was connected to a 1 mL syringe barrel used as reservoir. To rehydrate the slide, each channel was washed with 1 mL of PBS containing 1 mg/mL bovine serum albumin and 0.05% TWEEN®–20 (PBSTB) at 0.8 mL/min. Samples (0.1 mL Cy5-labeled cells in PBSTB) were then injected into appropriate channels and allowed to incubate for 1 hr at room temperature in the dark. Each channel was then washed with 1 mL of PBSTB at 0.3 mL/min. After removing the PDMS templates, the slides were washed with deionized water, dried under nitrogen, and imaged using the array biosensor.

Fluorescence imaging, data acquisition and analysis—Optical components of the Naval Research Laboratory's (NRL) array biosensor have been described in Feldstein et al., "Array Biosensor: Optical and Fluidics Systems," *J. Biomed. Microdevices* 1(2), 139-153 (1999) and Golden et al., "A comparison of imaging methods for use in an array biosensor," *Biosens. Bioelectron.* 17(9), 719-725 (2002). Briefly, it consists of a 635 nm, 12 mW diode laser for evanescent excitation of surface-bound fluorophores, a waveguide support, a GRIN lens array, several emission filters, and a Peltier-cooled charge-coupled device (CCD) imaging array. Digital images of the pattern of fluorescent spots were captured by the CCD and saved in Flexible Image Transport System (FTS) format. A custom data analysis software program (Sapsford et al., "Kinetics of Antigen Binding to Arrays of Antibodies in Different Sized Spots," *Anal. Chem.*, 73(22), 5518-5524 (2001)) was used to extract data from the FTS file, calculate the mean fluorescence intensity within each array element, and subtract out localized background, resulting in a mean net fluorescence value for each array element. Limits of detection (LODs) were defined as the lowest concentration tested for which the mean net fluorescence values (n>3) are greater than three standard deviations above both negative control values and localized background values.

Figure 7:
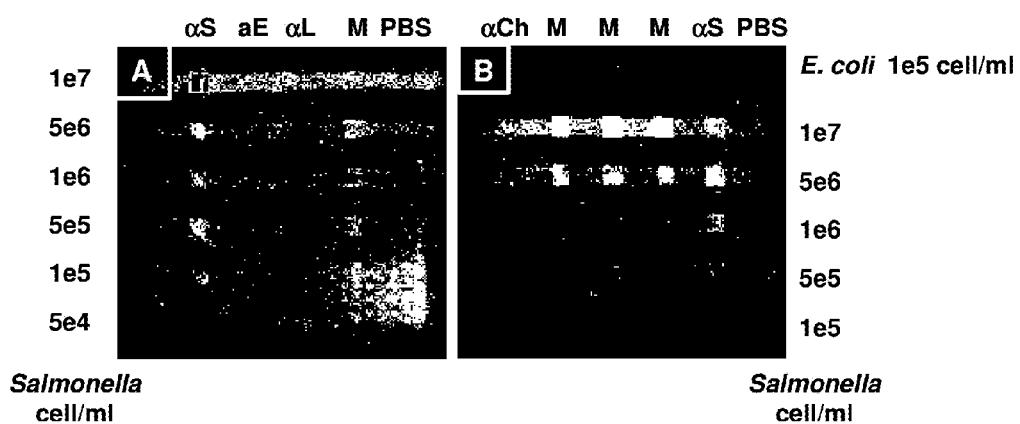
FIG. 7 shows charge-coupled device images of Cy5-labeled cells binding to immobilized magainin on sensing arrays.
Figure 8:
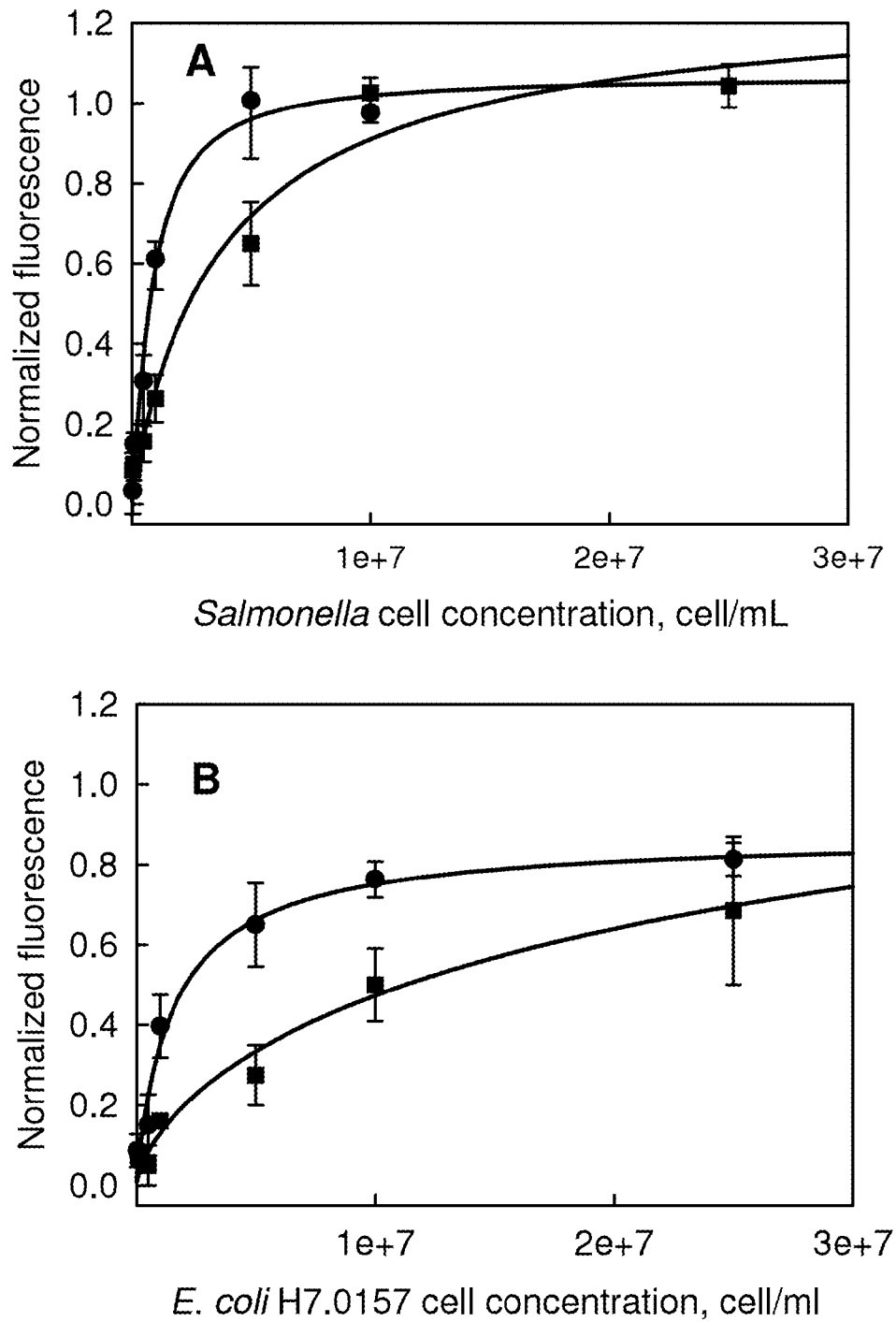
FIG. 8 shows concentration-dependence curves for Cy5-labeled *Salmonella* (A) and *E. coli* (B) cell binding to magainin immobilized by direct attachment through cross-linking chemistry with GMBS (●) and by avidin-biotin chemistry (■).

Fluorescently labeled, heat-killed *S. typhimurium* (FIG. 2) and *E. coli* O157:H7 were both detected on arrays where magainin I was immobilized via its C-terminal biotin and unmodified magainin I was immobilized by direct covalent attachment. In general, slides with directly immobilized magainin (FIG. 7, panel B) had lower levels of nonspecific binding, lower backgrounds, and higher signals from fluorescent bacteria bound to the peptide spots than avidin-coated slides patterned with C-terminal biotin-magainin (FIG. 7, panel A, P <0.05). Since the calculations for detection limits were based on both specific and nonspecific binding and variability thereof, both *E. coli* and *S. typhimurium* could be detected at significantly lower levels where magainin I had been immobilized directly (FIG. 8). Detection limits for labelled *E. coli* and *S. typhimurium* on covalently immobilized magainin I were $1.6 \times 10^5$ cell/mL and $6.5 \times 10^4$ cell/mL, respectively; detection limits on surfaces where magainin I was immobilized via its C-terminal biotin were at least 4-fold higher $-6.8 \times 10^5$ cell/mL and $5.6 \times 10^5$ cell/mL, respectively. Although sensitivity for *E. coli* was an order of magnitude poorer in magainin-based assays than analogous, optimized antibody-based assays (L. Shriver-Lake, personal communication), the LOD for *Salmonella* was in the same range as determined previously with the antibody used here as a control.

Figure 9:
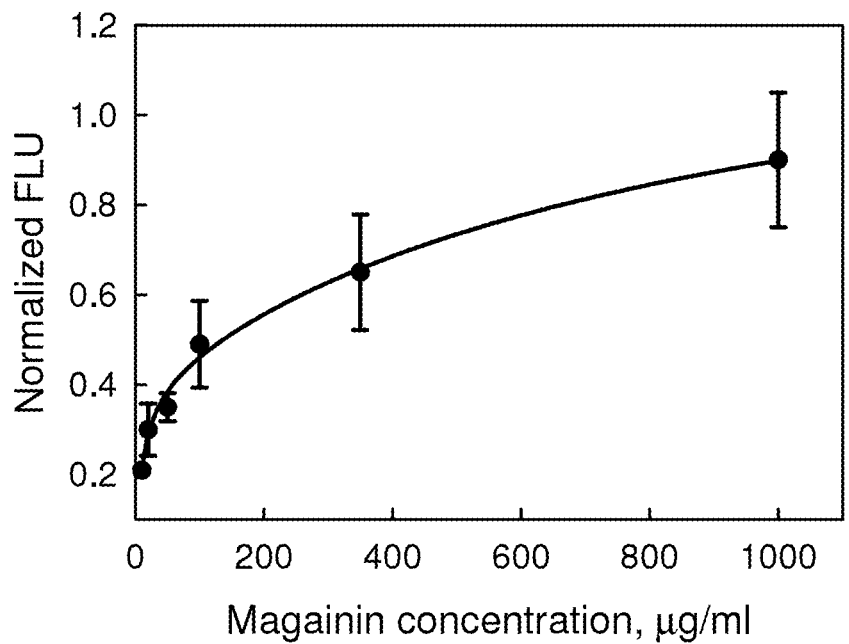
FIG. 9 shows binding of Cy5-labeled *Salmonella* ($1\times10^7$ cell/mL) to different densities of C-terminal biotinylated magainin.

The ability to capture target bacteria was strongly dependent on the density of immobilized magainin on the sensor surface (FIG. 9). Bacterial binding to control antibodies saturated at approximately 60 nM antibody in the patterning solution, independent of whether immobilization was direct or via avidin-biotin interactions. However, the AMP-based assays required significantly higher concentrations of magainin in solution during the immobilization step before saturation was observed (0.4 mM); this effect was observed with both C-terminal biotinylated magainin I and magainin immobilized covalently. This difference in concentrations required to achieve optimal surface density was not explained by the 80-fold difference in molecular size.

Although bacterial binding was demonstrated to magainin I immobilized directly and via a C-terminal biotin, no binding of either labeled species was observed to immobilized magainin biotinylated using an amine-specific biotin. As the initial interaction of α-helical AMPs with membranes of target bacteria is postulated to occur through binding of positively charged amino acids on the AMP with negatively charged phospholipids in the bacterial membrane, the lack of binding activity observed in these studies may well have been due to modification of an amine-containing residue critical to this initial process. This postulate was supported by the ability of magainin with a C-terminal biotin to bind cells, albeit at a lower level than magainin immobilized directly. The potential for modification of an essential amine moiety was further exacerbated by modification of multiple residues by the amine-specific biotin. In spite of the 1:1 molar ratio (biotin: magainin I) used in the labeling reaction, peptides with molecular weights corresponding to incorporation of one, two, and three biotins were observed through electrospray mass spectrometry. A similar over-labeling phenomenon has also been observed with the polymyxin family of AMPs, with consequent loss of microbial binding activity.

This study showed that characteristics of surface chemistry commonly considered as disadvantages in other systems (e.g., lack of diffusion and steric hindrance) worked to advantage when immobilizing a small peptide for detection of bacterial species. As the majority of amine moieties targeted by the cross-linker reside in the amino-terminal domain of magainin, the domain presumed responsible for the initial interaction with microbial membranes, a decrease in binding activity of the immobilized species (versus unmodified and free in solution) was not unexpected; furthermore, as others have shown that net charge on magainin greatly affect its activity, modification of these charged residues was also assumed to adversely affect binding activity. Therefore, it was surprising that magainin I immobilized via its C-terminal biotin (with native +4 charge) did not bind bacterial cells as well as magainin immobilized directly using an amine-specific crosslinker. It is believed that steric hindrance encountered during the direct immobilization procedure may have prevented modification of residues essential for target binding, as well as prevented modification of multiple sites. Such over-labeling was observed when magainin I was reacted (in solution) with an amine-reactive biotin; a similar phenomenon was observed with other amine-rich AMPs. Moreover, it is possible that the orientation of the directly immobilized magainin is optimal for target binding. It is not determined which amino acid residues are directly linked to the surface.

Furthermore, the binding activity of magainin may have been improved by the higher surface density when immobilized directly. Binding of labeled cells was observed when high concentrations of magainin were immobilized onto surfaces through direct covalent attachment or via a biotin moiety on the C-terminal amino acid. The two-fold higher potential packing density of surfaces with directly immobilized magainin immobilized directly versus magainin immobilized via its C-terminal biotin (assuming helical conformation for magainin and 20-30 Å between biotin binding sites on avidin), may have endowed these surfaces with sufficient avidity to detect bacterial targets at lower concentrations. In addition, given the high concentrations of magainin (~0.4 mM) required for optimal binding activity, formation of peptide multilayers was probable for both surfaces. However, it is possible that the conformation and/or orientation of magainin molecules immobilized directly more effectively promoted formation of peptide multilayers. Peptide-peptide interactions have been postulated to be required for strong target binding and microbicidal activity.

To date, there have been limited reports describing use of individual AMPs for capture and detection of target analytes. James et al., "Detection of Endotoxin Using an Evanescent Wave Fiber-Optic Biosensor," *Appl. Biochem. Biotechnol.*, 60(3), 189-202 (1996) describe used of polymyxin B as a capture molecule on a fiber optic biosensor for detection and quantification of *E. coli* lipopolysaccharide (LPS) in 5-minute competitive assays. The detection limit in these polymyxin B-based assays, approx. 10 ng/mL, calculates to approximately the same number of bacteria per mL ($3 \times 10^5$-$1.3 \times 10^6$ cells/mL) as observed with magainin I in these studies, assuming LPS monomer molecular weight of LPS between 4 and 20 kDa, and $1.2 \times 10^6$ LPS molecules per cell; magainin has also been observed to bind to LPS. A report has recently been published describing use of cecropin P1, another amphipathic α-helical AMP, to immobilize *E. coli* cells onto microtitre plates. (Gregory et al, "Immobilization of Escherichia coli cells by use of the antimicrobial peptide cecropin P1," *Appl. Environ. Microbiol.*, 71(3), 1130-1134 (2005).) As the thrust of this latter study was bacterial enrichment, the total analysis time (2.5 hours) and detection limits (~$10^7$ cfu/mL) were significantly different from those obtained in the present study.

EXAMPLE 2

Figure 10:
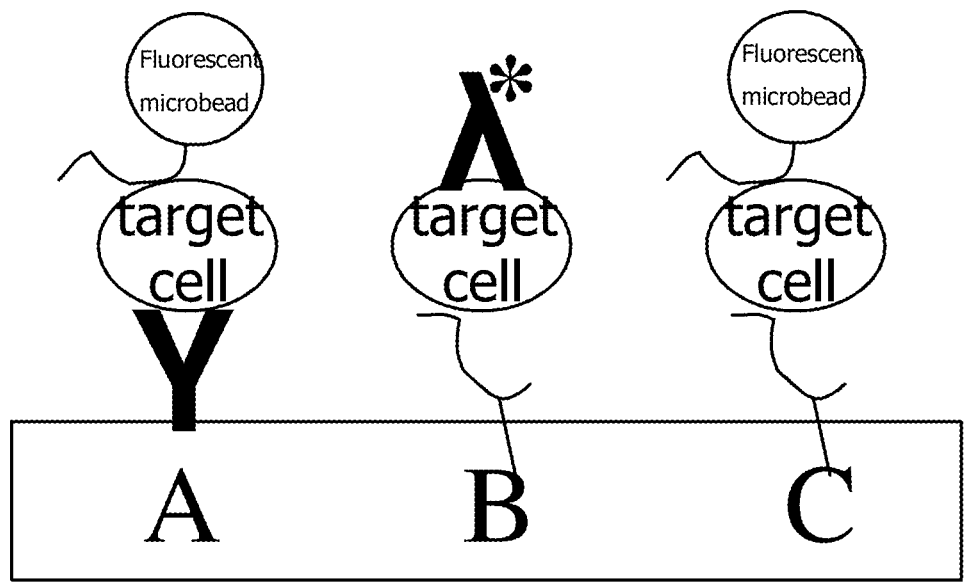
FIG. 10 shows formats for LUMINEX® based detection.
Figure 11:
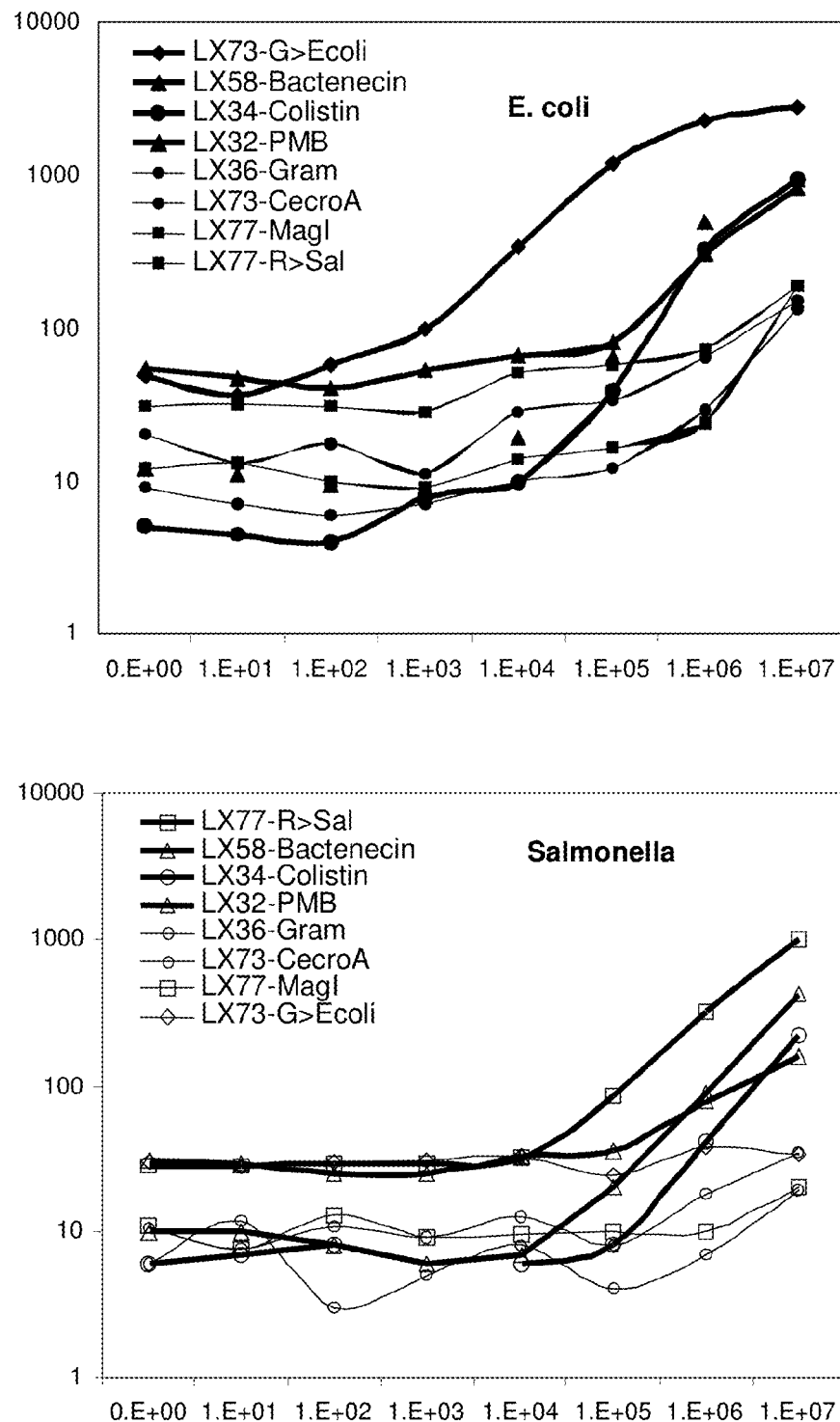
FIG. 11 shows detection of *E. coli* and *Salmonella*—LUMINEX®. Capture using AMP-derivatized Lx beads; antibody tracers.

LUMINEX®—"Sandwich"—type LUMINEX® assays had been developed, using antibodies for target capture (initial recognition) and AMPs for detection of bound targets (FIG. 10, format A). Development of AMP—capture assays for LUMINEX® (FIG. 10, format B) has begun; these results from LUMINEX® should be more comparable to those from the Array Biosensor for which AMP—capture assays have been developed. To date, this system has successfully shown capture of *E. coli, Salmonella*, and bot toxoid A using AM—derivatized LUMINEX® beads (FIG. 11). Although LODs for *E. coli* and *Salmonella* were the same as those obtained in antibody-based LUMINEX® assays ($10^2$-$10^3$ on bactenecin and $10^5$ cfu/ml on PMB, respectively), bot toxoid A could be detected only at extremely high concentrations (1 μg/ml); these latter results contrast greatly with results obtained using the Array Biosensor. Neither *Y. pestis* nor *Coxiella* could be detected at the concentrations tested on Lu LUMINEX® minex using AMP—coated LUMINEX® beads for capture.

These AMP capture assays have been modified to include AM—NR beads as tracers (FIG. 10, format C). However, large increases in background signals have been observed in these AMP—AMP assays, due to the AMP—NR beads binding non-specifically to AMP—derivatized LUMINEX® beads; the high background signals have to date prevented measurement of any significant signals above background values. In spite of these preliminary results, it is anticipated that use of additional blockers, chaotropes, and/or higher salt concentrations will lead to improvements in the AMP—AMP assays. Furthermore, it is believed that generic use of AMP—derivatized beads (Nile Red beads, magnetic beads) may lead to further improvements in both LUMINEX® and Array Biosensor.

Binding patterns —Above, differences in binding between *E. coli* and *Salmonella*, two very closely related species, using AMP tracer beads in LUMINEX® assays are demonstrated. This was extended to include additional species on LUMINEX® using AMP tracers (FIG. 12) and as well as AMP—Lx beads for capture (FIG. 13). Similar results have been observed in the Array Biosensor (FIG. 14). Several particularly noteworthy observations have been made with regard to binding patterns. Bot toxoids A and B, antigenically similar proteins, bind to different AMPs. The binding affinities for melittin in the assays run contrary to the hypothesis that inhibition of bot toxins by various AMPs is most likely caused by AMP binding to active sites. Melittin contains the KR sequence required for cleavage by bot toxin A peptidase activity, but is bound preferentially by toxoid B; conversely, cecropin A is bound preferentially by toxoid A, but does not contain any of the sequences required for cleavage by toxin A peptidase activity. Another interesting observation was that killed *E. coli* O157:H7 bound to a different subset of AMPs than a non-pathogenic strain, ATCC 35218; a similar difference in affinity for cecropin P1 between *E. coli* O157:H7 and a non-pathogenic strain was noted by Gregory, Id.

These AMP capture assays have been modified to include AMP-NR beads as tracers (FIG. 10, format C). However, large increases in background signals have been observed in these AMP-AMP assays, due to the AMP-NR beads binding non-specifically to AMP-derivatized Luminex beads; the high background signals have to date prevented measurement of any significant signals above background values. In spite of these preliminary results, it is anticipated that use of additional blockers, chaotropes, and/or higher salt concentrations will lead to improvements in the AMP-AMP assays. Furthermore, it is believed that generic use of AMP-derivatized beads (Nile Red beads, magnetic beads) may lead to further improvements in both Luminex and Array Biosensor.

EXAMPLE 3

Binding patterns—Above, differences in binding between *E. coli* and *Salmonella*, two very closely related species, using AMP tracer beads in Luminex assays are demonstrated. This was extended to include additional species on Luminex using AMP tracers (FIG. 12) and as well as AMP-Lx beads for capture (FIG. 13). Similar results have been observed in the Array Biosensor (FIG. 14). Several particularly noteworthy observations have been made with regard to binding patterns. Bot toxoids A and B, antigenically similar proteins, bind to different AMPs. The binding affinities for melittin in the assays run contrary to the hypothesis that inhibition of bot toxins by various AMPs is most likely caused by AMP binding to active sites. Melittin contains the KR sequence required for cleavage by bot toxin A peptidase activity, but is bound preferentially by toxoid B; conversely, cecropin A is bound preferentially by toxoid A, but does not contain any of the sequences required for cleavage by toxin A peptidase activity. Another interesting observation was that killed *E. coli* O157:H7 bound to a different subset of AMPs than a non-pathogenic strain, ATCC 35218; a similar difference in affinity for cecropin P1 between *E. coli* O157:H7 and a non-pathogenic strain was noted by Gregory, Id.

The effects of contaminating species on detection and identification of target species have been assessed. Specifically, an excess of *E. coli* O157:H7 was spiked into solutions of bot toxoid B and analyzed in Array Biosensor arrays, using antibody directed against botulinum toxin as a tracer; therefore, only binding of bot toxoid B would be detected. Although a small decrease in binding activity was observed, this difference was not statistically significant and the limit of detection on melittin (≤5 ng/ml) was not affected. However, at present, the only data analysis used for pattern recognition is normalization to a single AMP. This methodology does not yet take into account differences in binding due to varying target concentrations.

Obviously, many modifications and variations of the present invention are possible in light of the above teachings. It is therefore to be understood that the claimed invention may be practiced otherwise than as specifically described. Any reference to claim elements in the singular, e.g., using the articles "a," "an," "the," or "said" is not construed as limiting the element to the singular.

What is claimed is:

1. A device comprising:
one or more substrates;
wherein the substrates are a plurality of microspheres; and
a plurality of capture species independently selected from the group consisting of antimicrobial peptides, cytotoxic peptides, antibiotics, and combinations thereof;
wherein the capture species are bound to the substrates;
wherein separate subsets of microspheres comprise different capture species or combinations thereof, the microspheres of each subset encoded by a different ratio of two dyes; and
wherein at least two of the capture species are capable of multi-specific binding to one or more biological targets.

2. The device of claim 1, wherein at least two of the capture species have overlapping but not identical affinity properties.

3. The device of claim 1, wherein a majority of the capture species are capable of multi-specific binding.

4. The device of claim 1, wherein the device is a biosensor.

5. The device of claim 1, wherein the biological target is selected from the group consisting of bacteria, fungi, viruses, rickettsiae, toxins, and combinations thereof.

6. The device of claim 1, wherein the biological target is a toxin.

7. The device of claim 1, wherein the capture species are selected from the group consisting of alamethicin, peptaibols, apidaecin, bacitracin, bactenecins, bombinin, brevinin, buforins, cathelicidins, cecropins, cepaphalosporins, cytolysins, dermaseptins, defensins, esculentins, gramicidins, hemolysins, histatin, indolicidins, beta-lactams, lactoferricin, nisin, lantibiotics, magainins, mastoparans, melittin, moricin, parasin, pediocin, penicillins, polymyxins, protegrins, ranalexin, streptogamins, tachyplesins, teichoplanin, thionins, vancomycin, vibriolysins, derivatives thereof, and combinations thereof.

8. The device of claim 1, wherein the capture species include at least one naturally occurring peptide.

9. The device of claim 1, wherein the capture species are covalently bound to the substrates.

10. The device of claim 1, further comprising:
a source of one or more tracer species comprising a recognition element capable of binding to the at least one biological targets and a signal generating element.

11. The device of claim 10, wherein the signal generating element is selected from the group consisting of fluorophores, chromophores, fluorophore-labeled species, chromophore-labeled species, fluorescent nanospheres or microspheres, an enzyme or catalyst capable of producing an opto-electronic signal, and fluorescent nanospheres or microspheres coated with one of the capture species.

12. The device of claim 11, wherein the fluorophore-label is selected from the group consisting of Cy3, Cy5, cyanine dyes, phycobili proteins, and fluorescent protein.

13. The device of claim 1, further comprising:
a detector capable of independently detecting the presence of the tracer species or the biological target bound to each capture species to generate a binding pattern.

14. The device of claim 1, further comprising:
a detector selected from the group consisting of opto-electronic, surface plasmon resonance, interferometry, and quartz crystalline microbalance.

15. A device comprising:
one or more substrates; and
a plurality of capture species independently selected from the group consisting of antimicrobial peptides, cytotoxic peptides, antibiotics, and combinations thereof;
wherein the capture species are non-covalently bound to the substrate;
wherein at least two of the capture species are capable of multi-specific binding to one or more biological targets.

16. The device of claim 15, wherein at least two of the capture species have overlapping but not identical affinity properties.

17. The device of claim 15, wherein a majority of the capture species are capable of multi-specific binding.

18. The device of claim 15, wherein the device is a biosensor.

19. The device of claim 15, wherein the capture species are selected from the group consisting of alamethicin, peptaibols, apidaecin, bacitracin, bactenecins, bombinin, brevinin, buforins, cathelicidins, cecropins, cepaphalosporins, cytolysins, dermaseptins, defensins, esculentins, gramicidins, hemolysins, histatin, indolicidins, beta-lactams, lactoferricin, nisin, lantibiotics, magainins, mastoparans, melittin, moricin, parasin, pediocin, penicillins, polymyxins, protegrins, ranalexin, streptogamins, tachyplesins, teichoplanin, thionins, vancomycin, vibriolysins, derivatives thereof, and combinations thereof.

20. The device of claim 15, wherein the capture species include at least one naturally occurring peptide.

21. The device of claim 15, further comprising:
a source of one or more tracer species comprising a recognition element capable of binding to the at least one biological targets and a signal generating element.

22. The device of claim 21, wherein the signal generating element is selected from the group consisting of fluorophores, chromophores, fluorophore-labeled species, chromophore-labeled species, fluorescent nanospheres or microspheres, an enzyme or catalyst capable of producing an opto-electronic signal, and fluorescent nanospheres or microspheres coated with one of the capture species.

23. The device of claim 22, wherein the fluorophore-label is selected from the group consisting of Cy3, Cy5, cyanine dyes, phycobili proteins, and fluorescent protein.

24. The device of claim 15, further comprising:
a detector capable of independently detecting the presence of the tracer species or the biological target bound to each capture species to generate a binding pattern.

* * * * *

SEQUENCE LISTING

<160> NUMBER OF SEQ ID NOS: 17

<210> SEQ ID NO 1
<211> LENGTH: 20
<212> TYPE: PRT
<213> ORGANISM: Trichoderma viride -continued

```
<220> FEATURE:
<221> NAME/KEY: MOD_RES
<222> LOCATION: (1)..(1)
<223> OTHER INFORMATION: ACETYLATIONMETHYLATIONmethylalanine
<220> FEATURE:
<221> NAME/KEY: MOD_RES
<222> LOCATION: (3)..(3)
<223> OTHER INFORMATION: METHYLATIONmethylalanine
<220> FEATURE:
<221> NAME/KEY: MOD_RES
<222> LOCATION: (5)..(5)
<223> OTHER INFORMATION: METHYLATIONmethylalanine
<220> FEATURE:
<221> NAME/KEY: MOD_RES
<222> LOCATION: (8)..(8)
<223> OTHER INFORMATION: METHYLATIONmethylalanine
<220> FEATURE:
<221> NAME/KEY: MOD_RES
<222> LOCATION: (10)..(10)
<223> OTHER INFORMATION: METHYLATIONmethylalanine
<220> FEATURE:
<221> NAME/KEY: MOD_RES
<222> LOCATION: (13)..(13)
<223> OTHER INFORMATION: METHYLATIONmethylalanine
<220> FEATURE:
<221> NAME/KEY: MOD_RES
<222> LOCATION: (16)..(16)
<223> OTHER INFORMATION: METHYLATIONmethylalanine
<220> FEATURE:
<221> NAME/KEY: MOD_RES
<222> LOCATION: (17)..(17)
<223> OTHER INFORMATION: METHYLATIONmethylalanine
<220> FEATURE:
<221> NAME/KEY: MOD_RES
<222> LOCATION: (20)..(20)
<223> OTHER INFORMATION: amino alcohol of phenylalanine

<400> SEQUENCE: 1

Xaa Pro Xaa Ala Xaa Ala Gln Xaa Val Xaa Gly Leu Xaa Pro Val Xaa
1               5                   10                  15

Xaa Glu Gln Xaa
            20

<210> SEQ ID NO 2
<211> LENGTH: 10
<212> TYPE: PRT
<213> ORGANISM: Bacillus polymyxa
<220> FEATURE:
<221> NAME/KEY: LIPID
<222> LOCATION: (1)..(1)
<220> FEATURE:
<221> NAME/KEY: MOD_RES
<222> LOCATION: (1)..(1)
<223> OTHER INFORMATION: Dbu
<220> FEATURE:
<221> NAME/KEY: MOD_RES
<222> LOCATION: (3)..(3)
<223> OTHER INFORMATION: Dbu
<220> FEATURE:
<221> NAME/KEY: MOD_RES
<222> LOCATION: (4)..(4)
<223> OTHER INFORMATION: Dbu
<220> FEATURE:
<221> NAME/KEY: SITE
<222> LOCATION: (5)..(10)
<223> OTHER INFORMATION: Dbu amino group bound to C-terminal of Thr
<220> FEATURE:
<221> NAME/KEY: MOD_RES
<222> LOCATION: (5)..(5)
<223> OTHER INFORMATION: Dbu
<220> FEATURE:
<221> NAME/KEY: MOD_RES
<222> LOCATION: (8)..(8)
<223> OTHER INFORMATION: Dbu
```

```
<220> FEATURE:
<221> NAME/KEY: MOD_RES
<222> LOCATION: (9)..(9)
<223> OTHER INFORMATION: Dbu

<400> SEQUENCE: 2

Xaa Thr Xaa Xaa Xaa Phe Leu Xaa Xaa Thr
1               5                   10

<210> SEQ ID NO 3
<211> LENGTH: 10
<212> TYPE: PRT
<213> ORGANISM: Bacillus polymyxa
<220> FEATURE:
<221> NAME/KEY: LIPID
<222> LOCATION: (1)..(1)
<220> FEATURE:
<221> NAME/KEY: MOD_RES
<222> LOCATION: (1)..(1)
<223> OTHER INFORMATION: Dbu
<220> FEATURE:
<221> NAME/KEY: MOD_RES
<222> LOCATION: (3)..(3)
<223> OTHER INFORMATION: Dbu
<220> FEATURE:
<221> NAME/KEY: MOD_RES
<222> LOCATION: (4)..(4)
<223> OTHER INFORMATION: Dbu
<220> FEATURE:
<221> NAME/KEY: SITE
<222> LOCATION: (5)..(10)
<223> OTHER INFORMATION: Dbu amino group bound to C-terminal of Thr
<220> FEATURE:
<221> NAME/KEY: MOD_RES
<222> LOCATION: (5)..(5)
<223> OTHER INFORMATION: Dbu
<220> FEATURE:
<221> NAME/KEY: MOD_RES
<222> LOCATION: (8)..(8)
<223> OTHER INFORMATION: Dbu
<220> FEATURE:
<221> NAME/KEY: MOD_RES
<222> LOCATION: (9)..(9)
<223> OTHER INFORMATION: Dbu

<400> SEQUENCE: 3

Xaa Thr Xaa Xaa Xaa Leu Leu Xaa Xaa Thr
1               5                   10

<210> SEQ ID NO 4
<211> LENGTH: 15
<212> TYPE: PRT
<213> ORGANISM: Bacillus brevis
<220> FEATURE:
<221> NAME/KEY: MOD_RES
<222> LOCATION: (1)..(1)
<223> OTHER INFORMATION: FORMYLATIONVal or Ile

<400> SEQUENCE: 4

Xaa Gly Ala Leu Ala Val Val Val Trp Leu Trp Leu Trp Leu Trp
1               5                   10                  15

<210> SEQ ID NO 5
<211> LENGTH: 12
<212> TYPE: PRT
<213> ORGANISM: Bacillus subtilis
<220> FEATURE:
<221> NAME/KEY: SITE
<222> LOCATION: (1)..(2)
<223> OTHER INFORMATION: Acid group of Ile loses OOH and the C binds to
      both the amino and thiol groups of Cys
```

```
<220> FEATURE:
<221> NAME/KEY: SITE
<222> LOCATION: (6)..(12)
<223> OTHER INFORMATION: b-amino in Lys bound to Asne-amino in Lys bound
      to Ile
<220> FEATURE:
<221> NAME/KEY: MOD_RES
<222> LOCATION: (7)..(7)
<223> OTHER INFORMATION: Orn

<400> SEQUENCE: 5

Ile Cys Leu Glu Ile Lys Xaa Ile Phe His Asp Asn
1               5                   10

<210> SEQ ID NO 6
<211> LENGTH: 21
<212> TYPE: PRT
<213> ORGANISM: Bufo bufo

<400> SEQUENCE: 6

Thr Arg Ser Ser Arg Ala Gly Leu Gln Phe Pro Val Gly Arg Val His
1               5                   10                  15

Arg Leu Leu Arg Lys
            20

<210> SEQ ID NO 7
<211> LENGTH: 37
<212> TYPE: PRT
<213> ORGANISM: Hyalophora cecropia
<220> FEATURE:
<221> NAME/KEY: MOD_RES
<222> LOCATION: (37)..(37)
<223> OTHER INFORMATION: AMIDATION

<400> SEQUENCE: 7

Lys Trp Lys Leu Phe Lys Lys Ile Glu Lys Val Gly Gln Asn Ile Arg
1               5                   10                  15

Asp Gly Ile Ile Lys Ala Gly Pro Ala Val Ala Val Val Gly Gln Ala
                20                  25                  30

Thr Gln Ile Ala Lys
            35

<210> SEQ ID NO 8
<211> LENGTH: 35
<212> TYPE: PRT
<213> ORGANISM: Hyalophora cecropia

<400> SEQUENCE: 8

Lys Trp Lys Val Phe Lys Lys Ile Glu Lys Met Gly Arg Asn Ile Arg
1               5                   10                  15

Asn Gly Ile Val Lys Ala Gly Pro Ala Ile Ala Val Leu Gly Glu Ala
                20                  25                  30

Lys Ala Leu
        35

<210> SEQ ID NO 9
<211> LENGTH: 31
<212> TYPE: PRT
<213> ORGANISM: Sus scrofa
```

```
<400> SEQUENCE: 9

Ser Trp Leu Ser Lys Thr Ala Lys Lys Leu Glu Asn Ser Ala Lys Lys
1               5                   10                  15

Arg Ile Ser Glu Gly Ile Ala Ile Ala Ile Gln Gly Gly Pro Arg
            20                  25                  30

<210> SEQ ID NO 10
<211> LENGTH: 20
<212> TYPE: PRT
<213> ORGANISM: Artificial Sequence
<220> FEATURE:
<223> OTHER INFORMATION: Amino acids 1-8 are from Hyalophora cecropia.
      Amino acids 13-20 are from Apis.
<220> FEATURE:
<221> NAME/KEY: MOD_RES
<222> LOCATION: (20)..(20)
<223> OTHER INFORMATION: AMIDATION

<400> SEQUENCE: 10

Lys Trp Lys Leu Phe Lys Lys Ile Gly Ile Gly Ala Val Leu Lys Val
1               5                   10                  15

Leu Thr Thr Gly
            20

<210> SEQ ID NO 11
<211> LENGTH: 34
<212> TYPE: PRT
<213> ORGANISM: Phyllomedusa bicolor

<400> SEQUENCE: 11

Ala Leu Trp Lys Thr Met Leu Lys Lys Leu Gly Thr Met Ala Leu His
1               5                   10                  15

Ala Gly Lys Ala Ala Leu Gly Ala Ala Ala Asp Thr Ile Ser Gln Gly
            20                  25                  30

Thr Gln

<210> SEQ ID NO 12
<211> LENGTH: 23
<212> TYPE: PRT
<213> ORGANISM: Xenopus laevis

<400> SEQUENCE: 12

Gly Ile Gly Lys Phe Leu His Ser Ala Gly Lys Phe Gly Lys Ala Phe
1               5                   10                  15

Val Gly Glu Ile Met Lys Ser
            20

<210> SEQ ID NO 13
<211> LENGTH: 23
<212> TYPE: PRT
<213> ORGANISM: Xenopus laevis
<220> FEATURE:
<221> NAME/KEY: MOD_RES
<222> LOCATION: (23)..(23)
<223> OTHER INFORMATION: AMIDATION

<400> SEQUENCE: 13

Gly Ile Gly Lys Phe Leu His Ser Ala Lys Lys Phe Gly Lys Ala Phe
1               5                   10                  15

Val Gly Glu Ile Met Asn Ser
            20
```

```
<210> SEQ ID NO 14
<211> LENGTH: 26
<212> TYPE: PRT
<213> ORGANISM: Apis
<220> FEATURE:
<221> NAME/KEY: MOD_RES
<222> LOCATION: (26)..(26)
<223> OTHER INFORMATION: AMIDATION

<400> SEQUENCE: 14

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 15
<211> LENGTH: 12
<212> TYPE: PRT
<213> ORGANISM: Bos taurus
<220> FEATURE:
<221> NAME/KEY: DISULFID
<222> LOCATION: (3)..(11)

<400> SEQUENCE: 15

Arg Leu Cys Arg Ile Val Val Ile Arg Val Cys Arg
1               5                   10

<210> SEQ ID NO 16
<211> LENGTH: 34
<212> TYPE: PRT
<213> ORGANISM: Streptococcus lactis
<220> FEATURE:
<221> NAME/KEY: MOD_RES
<222> LOCATION: (2)..(2)
<223> OTHER INFORMATION: 2,3-didehydrobutyrine
<220> FEATURE:
<221> NAME/KEY: THIOETH
<222> LOCATION: (3)..(7)
<220> FEATURE:
<221> NAME/KEY: MOD_RES
<222> LOCATION: (5)..(5)
<223> OTHER INFORMATION: 2,3-didehydroalanine
<220> FEATURE:
<221> NAME/KEY: THIOETH
<222> LOCATION: (8)..(11)
<220> FEATURE:
<221> NAME/KEY: MOD_RES
<222> LOCATION: (8)..(8)
<223> OTHER INFORMATION: Abu
<220> FEATURE:
<221> NAME/KEY: THIOETH
<222> LOCATION: (13)..(19)
<220> FEATURE:
<221> NAME/KEY: MOD_RES
<222> LOCATION: (13)..(13)
<223> OTHER INFORMATION: Abu
<220> FEATURE:
<221> NAME/KEY: THIOETH
<222> LOCATION: (23)..(26)
<220> FEATURE:
<221> NAME/KEY: MOD_RES
<222> LOCATION: (23)..(23)
<223> OTHER INFORMATION: Abu
<220> FEATURE:
<221> NAME/KEY: THIOETH
<222> LOCATION: (25)..(28)
<220> FEATURE:
<221> NAME/KEY: MOD_RES
<222> LOCATION: (25)..(25)
<223> OTHER INFORMATION: Abu
<220> FEATURE:
<221> NAME/KEY: MOD_RES
<222> LOCATION: (33)..(33)
<223> OTHER INFORMATION: 2,3-didehydroalanine
```

```
<400> SEQUENCE: 16

Ile Xaa Ala Ile Xaa Leu Ala Xaa Pro Gly Ala Lys Xaa Gly Leu Ala
1               5                   10                  15

Met Gly Ala Asn Met Lys Xaa Ala Xaa Ala His Ala Ser Ile His Val
                20                  25                  30

Xaa Lys

<210> SEQ ID NO 17
<211> LENGTH: 30
<212> TYPE: PRT
<213> ORGANISM: Homo sapiens
<220> FEATURE:
<221> NAME/KEY: DISULFID
<222> LOCATION: (2)..(30)
<220> FEATURE:
<221> NAME/KEY: DISULFID
<222> LOCATION: (4)..(19)
<220> FEATURE:
<221> NAME/KEY: DISULFID
<222> LOCATION: (9)..(29)

<400> SEQUENCE: 17

Ala Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
                20                  25                  30
```